(12) United States Patent
Birgy et al.

(10) Patent No.: US 7,579,603 B2
(45) Date of Patent: Aug. 25, 2009

(54) PARTICLE THERAPY DEVICE AND METHOD OF DESIGNING A RADIATION PATH

(75) Inventors: Denis Birgy, Grossenseebach (DE); Harald Breuninger, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 282 days.

(21) Appl. No.: 11/521,240

(22) Filed: Sep. 13, 2006

(65) Prior Publication Data

US 2007/0114464 A1    May 24, 2007

Related U.S. Application Data

(60) Provisional application No. 60/717,835, filed on Sep. 16, 2005.

(30) Foreign Application Priority Data

Sep. 16, 2005  (DE)  ...................... 10 2005 044 409

(51) Int. Cl.
*A61N 5/10* (2006.01)
(52) U.S. Cl. ...................... 250/492.1; 600/1
(58) Field of Classification Search .................. 250/398, 250/492.1, 492.3, 493.1, 505.1; 600/1
See application file for complete search history.

(56) References Cited

U.S. PATENT DOCUMENTS

| | | | | |
|---|---|---|---|---|
| 5,260,581 A | * | 11/1993 | Lesyna et al. | 250/492.3 |
| 5,895,926 A | * | 4/1999 | Britton et al. | 250/492.3 |
| 6,614,038 B1 | * | 9/2003 | Brand et al. | 250/492.3 |
| 6,800,866 B2 | * | 10/2004 | Amemiya et al. | 250/505.1 |
| 7,351,988 B2 | * | 4/2008 | Naumann et al. | 250/492.3 |
| 2002/0030164 A1 | * | 3/2002 | Akiyama et al. | 250/492.1 |
| 2004/0173763 A1 | * | 9/2004 | Moriyama et al. | 250/492.1 |
| 2004/0174958 A1 | * | 9/2004 | Moriyama et al. | 378/145 |
| 2004/0183033 A1 | * | 9/2004 | Moriyama et al. | 250/492.3 |
| 2004/0200982 A1 | * | 10/2004 | Moriyama et al. | 250/492.3 |
| 2004/0232356 A1 | * | 11/2004 | Norimine et al. | 250/492.3 |
| 2005/0029472 A1 | * | 2/2005 | Ueno et al. | 250/492.1 |
| 2005/0247890 A1 | * | 11/2005 | Norimine et al. | 250/492.3 |

(Continued)

FOREIGN PATENT DOCUMENTS

DE    10 2004 027 071 A1    1/2006

(Continued)

OTHER PUBLICATIONS

H. Blattmann, "Beam Delivery Systems for Charged Particles", Radiat. Environ. Biophys., (1992), 31: pp. 219-231.

(Continued)

*Primary Examiner*—David A Vanore
*Assistant Examiner*—Michael Maskell
(74) *Attorney, Agent, or Firm*—Brinks, Hofer, Gilson & Lione

(57) ABSTRACT

A particle therapy device and method of designing a radiation path is provided. The particle therapy device comprising an accelerator and particle beam delivery unit that accelerates particles and delivers particles to at least two irradiation positions. A control system monitors and directs the particle along a particle beam path. The control system comprising an assignment unit, at least one control unit disposed at one of the irradiation positions and an accelerator control unit.

22 Claims, 2 Drawing Sheets

U.S. PATENT DOCUMENTS

| | | | |
|---|---|---|---|
| 2006/0022152 A1* | 2/2006 | Natori et al. | 250/493.1 |
| 2006/0113487 A1* | 6/2006 | Naumann et al. | 250/492.3 |
| 2006/0118736 A1* | 6/2006 | Moriyama et al. | 250/493.1 |
| 2006/0219948 A1* | 10/2006 | Ueno et al. | 250/492.1 |
| 2007/0075273 A1* | 4/2007 | Birgy et al. | 250/492.3 |
| 2007/0114471 A1* | 5/2007 | Birgy et al. | 250/505.1 |

FOREIGN PATENT DOCUMENTS

| | | |
|---|---|---|
| EP | 0 986 070 | 3/2000 |
| EP | 1 454 654 A2 | 9/2004 |
| EP | 1 454 657 A2 | 9/2004 |
| WO | WO 96/25201 | 8/1996 |

OTHER PUBLICATIONS

H. Blattmann, "Beam delivery systems for charged particles", Radiation and Environmental Biophysics; Springer-Verlag 1992; 31:219-231.

European Office Action dated Apr. 10, 2008 for EP 06 119 988.1-2319 with English translation.

\* cited by examiner

PARTICLE THERAPY DEVICE AND METHOD OF DESIGNING A RADIATION PATH

The present patent document claims the benefit of the filing date under 35 U.S.C. §119(e) of Provisional U.S. Patent Application Ser. No. 60/717,835, filed on Sep. 16, 2005, which is hereby incorporated by reference. This application also claims the benefit of DE 10 2005 044 409.1, filed Sep. 16, 2005.

BACKGROUND

1. Field

The present embodiments relate to a particle therapy device and method of designing a radiation path.

2. Related Art

A particle therapy device generally includes a particle acceleration unit, a particle beam delivery unit that is connected thereto, and a plurality of irradiation positions. The acceleration of the particles, for example, protons, pions, helium ions, carbon ions or oxygen ions, is done by a synchrotron or cyclotron. The accelerated high-energy particles are decoupled from the particle acceleration unit and directed into the particle beam delivery unit (also known as a high-energy beam transport system HEBT). For example, when using a synchrotron, a knock-out exciter decouples the high-energy particles from the particle acceleration unit. The HEBT delivers the high-energy particles to the irradiation position. The irradiation position is the location where the irradiation procedure is to take place.

For example, an irradiation position, which is also referred to as a treatment position below, is used to perform a tumor therapy of a patient. The patient is positioned in the particle beam path and exposed to the high-energy particles.

A distinction is made between a "fixed beam" treatment chamber and a "gantry-based" treatment chamber. A fixed beam treatment chamber has particles that impinge upon a treatment location from a fixed direction. In the gantry-based treatment chamber the particle beam is directed onto the treatment location of the gantry from different directions. The beam quality is monitored at an irradiation location referred to below as a checking location. Beam parameters such as particle energy, energy distribution, and beam intensity are monitored at the checking location by means of quality measurements.

Demanding requirements are placed on the safety of a particle therapy facility. For example, the particle beam must only be delivered to an irradiation position that is prepared for an irradiation procedure and has requested the particle beam. The particle beam must also have the correct requested parameters. Rapid interruption of the particle delivery is necessary in the event of an emergency. The HEBT, for example, features a baffle. The baffle allows the particle beam to be quickly cut off. A control and safety system of the particle therapy device is generally used to check and direct a particle beam having the required parameters into the relevant treatment chamber.

The required parameters are defined in the treatment plan (therapy plan). The treatment plan specifies how many particles should hit the patient, from what direction and with what energy. The energy of the particles determines the penetration depth of the particles into the patient. The location where the maximum interaction occurs with the tissue during the particle therapy is the location where the maximum dose of particles is deposited. The parameters required by the treatment plan are usually converted by an accelerator control unit into configuration parameters, for example, in the form of machine parameters, for the accelerator and particle beam delivery unit. The information describing the irradiation position to which the particle beam must be guided is converted into configuration parameters for the particle beam delivery unit. A control unit of the irradiation position controls a positioning device. The positioning device is dependent on the position of a patient who must be irradiated or phantom material which must be irradiated in relation to the particle beam.

A particle therapy facility including a plurality of fixed-beam treatment positions and a gantry is disclosed in EP 0 986 070. Various irradiation facilities and techniques are described by H. Blattmann in "Beam delivery systems for charged particles", Radiat. Environ. Biophys. (1992) 31:219-231. A method for selecting a treatment room is disclosed in U.S. Pat. No. 5,260,581 and a control and safety system for an irradiation therapy facility is disclosed in U.S. Pat. No. 5,895,926.

SUMMARY

In one exemplary embodiment, a particle therapy device includes an accelerator and particle beam delivery unit that accelerates particles and delivers the particles from the accelerator to at least one irradiation position. In one exemplary embodiment, a cyclotron or a synchrotron is used as an accelerator, into which possibly preaccelerated particles are coupled. The particle beam delivery takes place, for example, with the aid of at least one configurable element in the beam path. The element or elements are configured with the aid of the accelerator control unit according to the beam path that is required in each case. In one exemplary embodiment, configuration parameters required for configuration are transferred and stored in a temporary storage.

At least one of the treatment chambers or positions has a control unit directly connected to a signal input of the assignment unit via a direct and permanently (fixedly) assigned signal connection. The control unit is operable to emit a request signal via the signal connection in order to request a particle beam for an irradiation procedure, such that the presence of the request signal at the signal input unambiguously indicates the requesting irradiation position.

In one exemplary embodiment, between the assignment unit and the control unit of the irradiation position, there is a second permanently assigned signal connection that transfers a confirmation signal from a signal output of the assignment unit to the control unit.

In one exemplary embodiment, the therapy device has a plurality irradiation positions. Each of the plurality of irradiation positions is individually connected via a permanently assigned signal connection directly to one signal input (and possibly signal output) of the assignment unit. The control units are connected to the assignment unit via a direct hardware connection, for example, via individual direct signal lines.

In another exemplary embodiment, the accelerator and particle beam delivery unit have a plurality of elements. The plurality of elements are individually connected via one permanently assigned signal connection in each case directly to one signal output of the assignment unit in each case. The configurable elements are also connected to the assignment unit via a direct hardware connection, for example, via individual direct signal lines.

Examples of configurable elements include beam deflection magnets that divert the particle beam from the beam delivery system into the individual treatment rooms, a beam decoupling device of an accelerator, for example, a knock-out exciter of a synchrotron ring, a dipole magnet of a baffle in the HEBT. Possible configuration parameters are, for example, an applied magnetic field, a required current value which must be configured, or a HF decoupling frequency. A configurable element is preferably designed for processing and, depending on the presence of the activation signal, for implementing the at least one transferred configuration parameter. In one exemplary embodiment, the configurable element includes a buffer storage in which a transferred configuration parameter can be stored and read out following receipt of the activation signal.

In one exemplary embodiment, transfer of the configuration parameter takes place via a data bus system to which the accelerator control unit and the relevant element are attached. The configuration parameter is dependent on the irradiation procedure taking place at the irradiation position.

In one exemplary embodiment, at least one control unit of the irradiation positions is attached to this data bus system or to a dedicated data bus system in order to exchange parameters of the particle beam that are required for irradiation and/or parameters of the accelerator and particle beam delivery unit.

Examples of irradiation positions include a treatment position for radiation therapy, for example, a fixed-beam or gantry treatment position, or a test position for testing parameters which form the basis of the particle irradiation.

In another exemplary embodiment, the particle acceleration and/or forwarding of the particles can be interrupted by the assignment unit and/or the control unit in the event of an error. The activation signal must be continuously present for the configuration of the element. For example, if the activation signal is terminated, then the configuration is terminated. In one exemplary embodiment, the activation signal acts as a switch, and the element can be switched to "non-configurable".

The specific subdivision of the control and safety system into an assignment unit, at least one control unit arranged at one of the irradiation positions, and an accelerator control unit, allows the separation of the management and control of therapy-related procedures at the irradiation position and the management and control of all procedures and configurations in the accelerator and beam delivery unit.

For the safe operation of a particle therapy device, it is important that the particle beam is reliably delivered to only irradiation rooms prepared for the irradiation. The interconnected assignment unit provides a safe therapy device. In one exemplary embodiment, the interconnected assignment unit receives the request signals from the control units of the irradiation rooms, manages the sequence of irradiation procedures and assigns the particle beam to the requesting irradiation room if said particle beam is available. This communication takes place via the direct exchange of request and confirmation signals in the request phase. The transfer of information takes place in the configuration phase, for example, from the control unit via a bus system to the accelerator control unit. The accelerator control unit then transfers configuration parameters required for the irradiation procedure to those elements of the accelerator and beam delivery unit which determine the beam path. An implementation of the configuration parameters takes place if an activation signal from the assignment unit is present. The configuration parameters are transferred directly in the activation phase by the assignment unit to the configurable elements that are required for the corresponding beam path. The assignment unit is operable as a fail-safe control system that includes a memory and a look-up table that conveys which elements must be activated for which irradiation position. This activation step is separated from the accelerator control unit.

Use is preferably made of direct and permanently assigned signal connections. A direct and permanently assigned signal connection is a direct hardware connection, for example, an individual signal line that is preferably fail-safe. In this embodiment, "direct" also includes a plurality of cable sections being clamped together. In an alternative embodiment, a single continuously laid cable is used.

A direct and permanently assigned signal connection creates a definitive assignment of an irradiation position to a signal input. Accordingly, the correct irradiation position is always recognized by the assignment unit, without requiring a confirmation for verification of the correct irradiation position via, for example, a protocol. Thus, no additional verification acts are required. A hardware-coded and hardware-controlled approach allows a secure delivery of a particle beam along a particle path to the requesting irradiation position. In one exemplary embodiment, the signal connection is used in one direction, such that logic for distinguishing the direction of the signal transmission is not required, said logic being susceptible to failure.

The hardware-coding provides a secure assignment and/or secure beam-availability control via dedicated hardware signal lines that minimize the possibility of signal errors.

DETAILED DESCRIPTION

Figure 1:
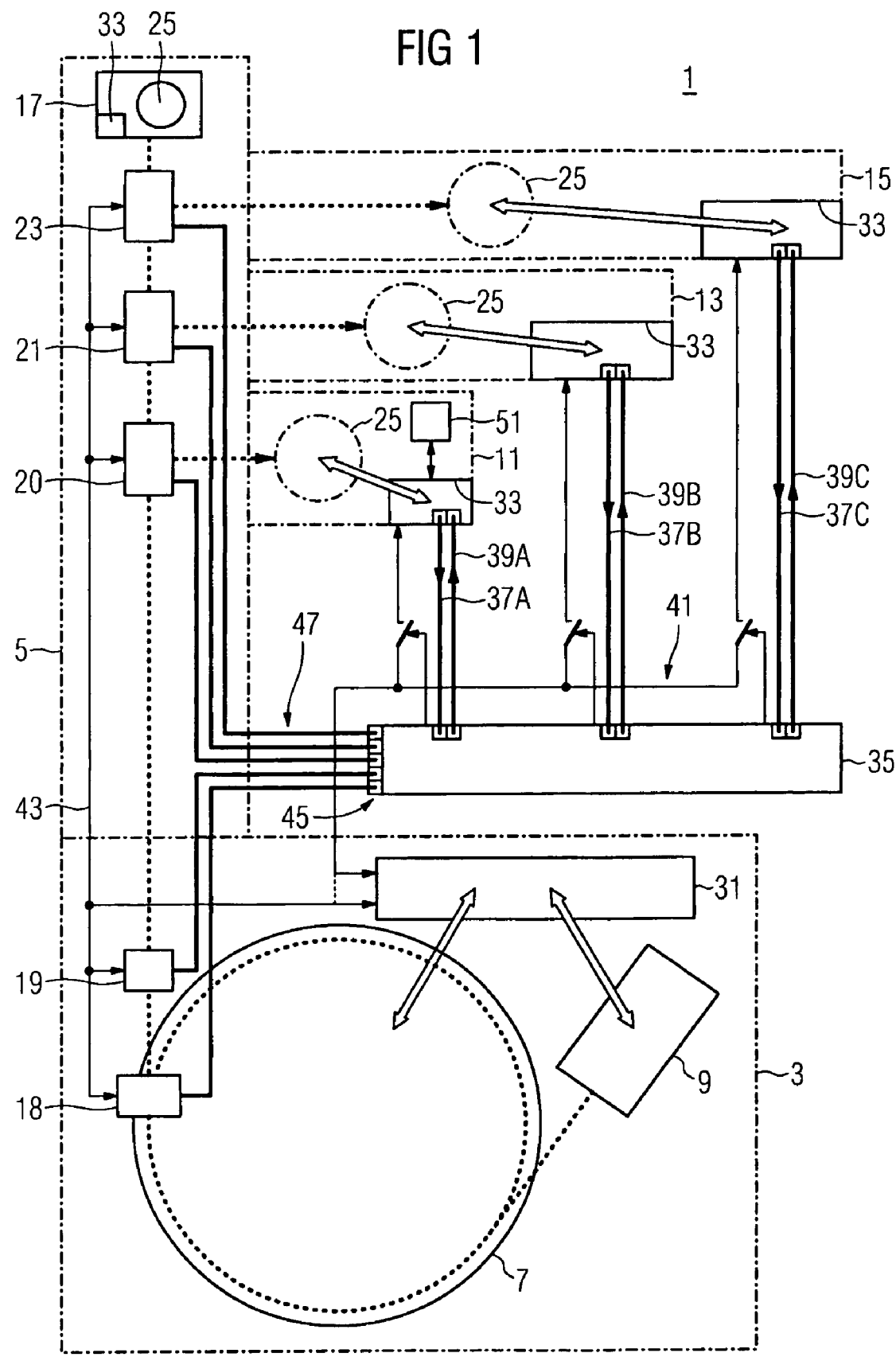
FIG. 1 illustrates an overview of an exemplary therapy device.

FIG. 1 illustrates an exemplary therapy device 1 and shows the interaction of various control units involved. The control units effect and monitor the configuration of components. A beam having corresponding parameters is sent to an irradiation position. For safety reasons, in this case important signals are transferred via hardware connections which are not susceptible to failure. In one exemplary embodiment, the hardware connection consists of a dedicated specific line and is unambiguously or separately assigned to the transmission of a signal.

The therapy device 1 features an accelerator unit 3 and a particle beam delivery unit 5. In one exemplary embodiment, a synchrotron 7 including a preconnected linear accelerator unit 9 is used as an accelerator. The beam delivery unit 5 distributes the particles over a plurality of irradiation positions. For example, three treatment positions 11, 13 and 15 for radiation therapy and a test position 17 that checks the quality of the particle beam are provided in the therapy device 1.

At the test position 17, it is possible to perform quality assurance with the aid of quality procedures. Quality procedures use regular tests for verification of the previously defined beam parameters relating to, for example, positional increments, intensity increments or particle energies. In one exemplary embodiment, the particle energies are contained in a library and are checked by automated Bragg peak measurements on phantom material.

Particles that are stored in the exemplary synchrotron ring 7 are decoupled using a decoupling device 18 and directed into the beam delivery unit 5. In one exemplary embodiment, a baffle 19 having three small dipole magnets is disposed after the decoupling unit 18. The baffle 19 allows a rapid beam cut-off following completion or interruption of the irradiation procedures is complete. For example, rapidly cutting off the central dipole destroys the beam on a collimator.

The delivery of the particles to the irradiation positions 11, 13 and 15 is achieved by diverting the particle beam using deflection magnets 20, 21 and 23 from a main beam direction in the beam delivery unit 5. The test position 17 is situated in the main beam direction. The interaction of the particles with a patient or a phantom material takes place in irradiation zones 25 at the irradiation positions. In one exemplary embodiment, one of the irradiation zones 25 is, for example, a maximal scannable scan area of a (raster) scanning device, a maximal scatter area which can be irradiated by a scatter device, or a configurable gantry irradiation area.

In one exemplary embodiment, the linear accelerator unit 9 includes at least one of a usable ion source, a low-energy beam transport, a radio-frequency quadrupole, a drift-tube accelerator or an injection beam transport. The task of the linear accelerator unit 9 is to generate one or more particle types. The linear accelerator also rids the particle types of contamination from unwanted particle types and configures the beam intensity in the low-energy range for the synchrotron, for example, to preaccelerate the particles and to prepare the particle beam. The particles are prepared with respect to the pulse length and the beam parameters according to the requests of the synchrotron.

In one exemplary embodiment, if the therapy device 1 is used for irradiation with scanning methods, a slow extraction of particles allows optimal utilization of the accelerated particles and precise beam monitoring during the scanning. In one exemplary embodiment, when using a synchrotron, a HF knock-out method is used for beam extraction. A knock-out exciter is used as the decoupling unit 18.

In one exemplary embodiment, the control and safety system of the therapy device 1 is divided into a plurality of components. A division of the plurality of components can be implemented differently. Alternatively, a division does not need to be implemented at all, provided the various aspects are taken into consideration during the monitoring.

In the exemplary embodiment according to FIG. 1, an accelerator control unit 31 ensures that the requested particle beam arrives according to its specification in the treatment room. Control units 33 are arranged at the irradiation positions and manage the execution of an irradiation procedure, for example, directing the particle beam to hit a patient in accordance with an irradiation schedule.

In one exemplary embodiment, the control and safety system includes an assignment unit 35 that assigns a particle beam to the irradiation position 11, 13, 15, 17 that requested it. The assignment unit 35 is connected on one side to the control units 33 and transfers a request signal via a permanent and uniquely assigned signal line 37A, 37B, 37C. In another exemplary embodiment, a permanently assigned signal line 39A, 39B, 39C is disposed between the assignment unit 35 and the control units 33. The permanently assigned signal line 39A, 39B, 39C transfers a confirmation signal from the assignment unit 35 to the irradiation position to which the particle beam will be delivered next.

The control and safety system includes at least one data bus system 41, to which the control units 33 and the accelerator control unit 31 are attached. The data bus system transfers configuration parameters for the accelerator unit 3 and the particle beam delivery unit 5 for the next irradiation to be carried out. The assignment unit 35 sends signals to the data bus system 41 in such a way that only that irradiation position 11, 13, 15, 17 that has received a confirmation signal can transfer parameters.

The accelerator control unit 31, and elements of the accelerator 3 and beam delivery unit 5 which are configured by said accelerator control unit 31, are linked to a second data bus system 43. In an alternate embodiment, the second data bus system is linked to the data bus 41 (broken-line connection). The elements linked to the second data bus system, according to exemplary FIG. 1, are the decoupling unit 18, the baffle 19 and the deflection magnets 20, 21, 23. In one exemplary embodiment, configuration parameters are required by these elements in order to configure the currently requested particle beam path and to transport the particles with the correct energy. The parameters are transferred to the elements via the data bus system 43. A beam path requires configurations of elements in the high-energy beam path depending on a specified irradiation position.

In one exemplary embodiment, implementation of the configuration parameters takes place if an activation signal from the assignment unit 35 is present at the element and properly configured. The configurable elements are connected to signal outputs 45 of the signal assignment unit 35 via direct permanently assigned signal lines 47.

The fact that request signals and/or activation signals are sent and received via specific unambiguous hardware connections is sufficient to ensure that the request signal was sent from a specific and known irradiation position and/or that only explicitly activated elements are configured for determining the beam path. Accordingly, signals will not be erroneously received from other irradiation positions or erroneously transferred to other elements.

According to the exemplary embodiment illustrated in FIG. 1, a safer routine for irradiating a patient is possible. The irradiation parameters, including the required parameters, for example, beam incidence direction, beam intensity, particle type, or particle energy is specified in a therapy schedule 51.

In one exemplary embodiment, once the irradiation schedule 51 for the patient is loaded at the irradiation position, all safety-related preconditions have been satisfied and the patient has been properly positioned, a therapy control system, for example, a control unit 33 of the irradiation positions 11, 13, 15, requests a beam having the scheduled parameters for the current irradiation position. In one alternate exemplary embodiment, it is only possible to use and request data records that have been tested and approved. The data records are stored and available in the accelerator control system 31.

In one exemplary embodiment, an operator initiates the transmission of a request signal from the control unit 33 of the irradiation position 11 along the direct, permanently assigned signal line 37A to the assignment unit 35. The assignment unit 35 checks the availability of the particle beam. If an irradiation procedure is still taking place at an adjacent irradiation position, the assignment unit 35 does not allocate the particle beam to the requesting treatment room until this irradiation procedure is complete. For example, once the particle beam is available, the assignment unit 35 enables the connection from the control unit 33 of the treatment room 11 to the accelerator control unit 31 in the data bus system 41 for the transfer of the desired parameters for the next irradiation procedure.

In one exemplary embodiment, the assignment unit 35 sends activation signals to the configurable elements that are required for the beam delivery to the requesting irradiation position via the permanently assigned signal lines 47. The configurable elements are, for example, the decoupling unit 18, the baffle 19 and the deflection magnet 20 The accelerator control unit 31 transfers configuration parameters to these elements. Only if the activation signal is present can the configuration parameters which are transferred from the accelerator control unit 31 be implemented in the elements and determine the required particle beam path.

The configurable elements are preferably deactivated by precedence. Only if an activation signal is present are corresponding currents, etc. configured. As broadly described herein, deactivation means that the default value "Current to zero" is configured. In this exemplary embodiment, to transfer an activation signal, a signal output of the assignment unit 35 is connected via a direct and permanently assigned signal connection to at least one of the configurable elements.

In one exemplary embodiment, only in conjunction with the activation signal can a transferred configuration parameter by implemented in the configurable element. For example, the activation signal must be present before and/or during the implementation. The accelerator control unit 31 acts as a locking mechanism, and configurable elements are deactivated by precedence. Corresponding currents are configured only if an activation signal is present. As broadly described herein, deactivation means, for example, that the default values are configured and there is no current flow in the magnet coils.

In this exemplary embodiment, once the configuration is complete, the assignment unit 35 transfers a confirmation signal along the direct connection line 39A. Following a possible confirmation of this signal by the treatment position 11, the delivery of particles takes place for irradiation in the irradiation area 25.

The sequence of configuration activities and signal transfers can be organized as required, with the exception of the presence of an activation signal for the actual implementation of physical configurations. In an alternative routine, the confirmation signal is transferred to the treatment room 11 along the connection line 39A immediately after the assignment of the particle beam to the treatment room 11. In one exemplary embodiment, a "Beam on" signal is initiated by the control unit 33 of the treatment room in response to the confirmation signal and triggers activation signals from the assignment unit 35 and the transfer of configuration parameters from the accelerator control unit 31 to the relevant elements. For example, the physical implementation of the configuration parameters in the elements takes place and the particles are delivered to the irradiation position. Implementation only takes place after transfer of the confirmation signal, and thus incorrect configuration is prevented at an early stage.

For example, in the event that a non-requesting control unit 33 receives a confirmation signal, a corresponding deactivation can take place automatically.

In one embodiment, the routine is divided into three stages. In a first stage, which concerns preparation, only the control unit 33 and the assignment unit 35 communicate (beam request signal, confirmation signal of the beam assignment and "Beam on" signal). In a second stage, which concerns configuration, the assignment control unit 35 and the accelerator control unit 31 communicates. For example, corresponding beam parameters are requested and the corresponding parameters are transferred to the elements and the accelerator unit. In a third stage, which concerns activation, the assignment unit 35 communicates directly with the elements and configures the required elements. The parameters transferred from the accelerator control unit are implemented. The third stage makes the configuration physically possible and implements it. In an alternate embodiment, the third stage takes place concurrently with the second stage.

In one exemplary embodiment, during the irradiation procedure, the therapy device 1 operates independently. For example, the control unit 33 manages scanner magnets and beam diagnosis units that monitor the beam quality. The only intervention that can be made by the operating staff is to terminate the irradiation procedure. If a beam termination is initiated or if another error is detected in the system, the assignment unit 35 uses the direct and permanently assigned signal lines to the configurable elements in order to withdraw the permission to be active. For example, in the event of such an error beam destruction occurs within the baffle 19 by shutting down a dipole magnetic field. The deflection magnets 20, 21, 23 are switched to zero current and the KO exciter is switched off.

In one exemplary embodiment, the configurable elements are reset to their default values after the completion of an irradiation procedure; for example, the deflection and/or baffle magnetic fields are set to zero or the KO frequency is switched off. In one exemplary embodiment, the therapy device includes an utilization-optimizing operating system that manages irradiation procedures that must be carried out. The operating system allows the therapy device to bypass a default value, for example, by managing the assignment unit 35. By bypassing a default value with regard to the irradiation procedure which will be performed next the beam path is, for example, more quickly available for the next irradiation procedure.

The tasks of the various components of the control and safety system for the beam request and beam path specification can be summarized as follows: The accelerator control unit 31 controls the correct values of the configuration parameters for the configurable elements in the accelerator and beam delivery unit. The assignment unit 35 ensures the configurability of these parameters by means of an activation process, in which specifically only those elements which are necessary for a beam path are activated. For this purpose, the assignment unit preferably has a stored table including the possible beam paths e.g. in a look-up table. In addition, the availability of the particle beam is checked within the assignment unit 35, which is preferably designed as a fail-safe stored-program control system. The particle beam is only allocated if it is available. The control units in the irradiation positions supply the data from the irradiation schedule and ultimately decide on the delivery of the beam, i.e. they trigger the beam delivery at the corresponding irradiation position.

The present embodiments are not limited to the use of direct and permanently assigned connections as shown in FIG. 1. For example, it is possible to embody solely the connection between one of the control units 33 and the assignment unit 35 in a way that provides a different configuration of elements.

Figure 2:
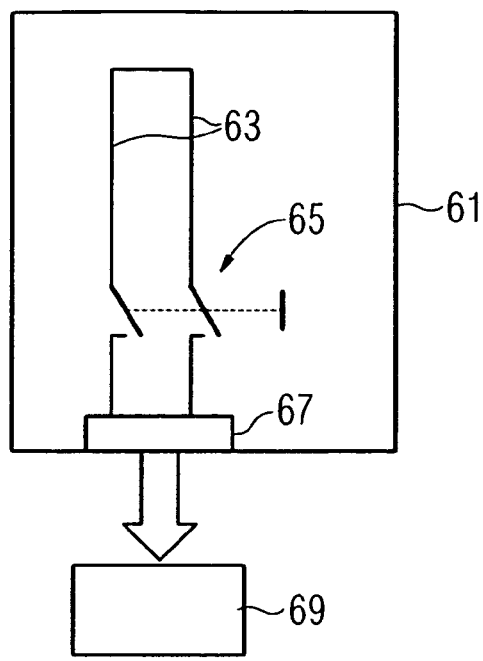
FIG. 2 illustrates a fail-safe switch unit according to one exemplary embodiment.
Figure 3:
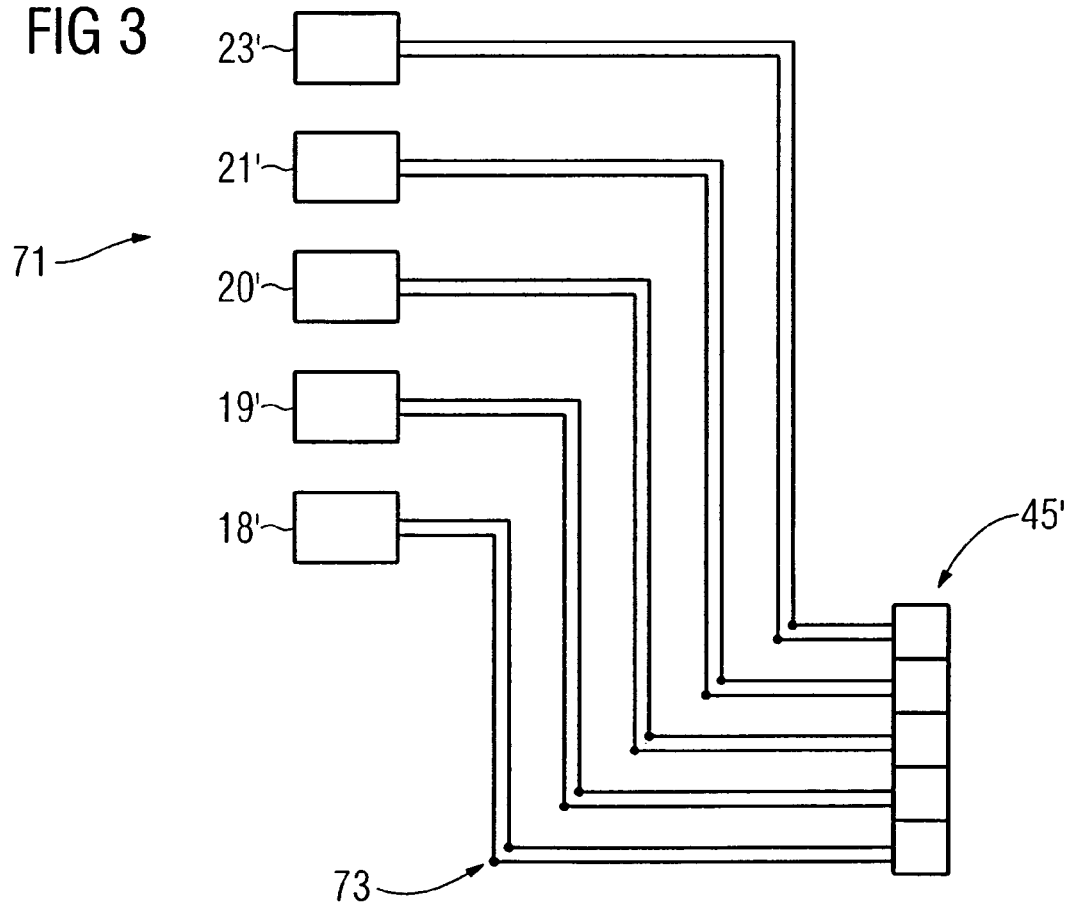
FIG. 3 illustrates fail-safe connections according to one exemplary embodiment.

FIGS. 2 and 3 illustrate features of a fail-safe direct connection. FIG. 2 illustrates a fail-safe switch unit 61 that is used, for example, in the control unit 33 and/or the assignment unit 35 for transferring a request signal, a confirmation signal and/or an activation signal. In one exemplary embodiment, two lines 63 are wired in parallel and connected to a signal output 67 via a switch 65 having a positive opening/closing. The switch 65 opens/closes the two lines 63 together. In one exemplary embodiment, the switch 65 assumes a open position in the event of an error. The signal output is connected to a unit 69. For example, with reference to FIG. 1, the unit 69 is one of the control units 33, the assignment unit 35 or one of the elements which can be activated such as the decoupling unit 18, the baffle 19 or one of the deflection magnets 20, 21, 23.

FIG. 3 illustrates the use of fail-safe dual lines for transferring activation signals to elements 71. The elements 71 are configurable, for example, according to FIG. 1, a decoupling unit 18', a chicane 19' or deflection magnets 20', 21', 23'. The elements 71 are connected via corresponding fail-safe switch units to signal outputs 45', which are part of the assignment unit 35 according to FIG. 1. The use of clamps 73 may be unavoidable due to the size of a therapy device 1.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A particle therapy device comprising:
an accelerator;
a particle beam delivery unit operable with the accelerator, the particle beam delivery unit operable to deliver particles to at least two irradiation positions; and
a control system configured to monitor the particles along a particle beam path, the control system comprising an assignment unit, at least one control unit disposed at one of the at least two irradiation positions and an accelerator control unit,
wherein the at least one control unit is configured to emit a request signal that requests a particle beam for an irradiation procedure,
wherein the assignment unit is configured to assign the particle beam path to the requesting irradiation position, and is connected to configurable elements that direct the beam path,
wherein only those configurable elements that are required for the beam path are selectively activated, and
wherein the accelerator control unit is configured to emit configuration parameters to the configurable elements, the assignment unit configured as a fail-safe control system such that the assignment unit sends an activation signal to the configurable elements of the beam path when setting up the particle beam path, the activation signal separate from the emission of configuration parameters from the accelerator control, the activation signal being present during the implementation of the configuration parameters and allowing the implementation of the configuration parameters.

2. The particle therapy device as claimed in claim 1, wherein the control unit is operable to transfer data from a treatment plan.

3. The particle therapy device as claimed in claim 2, wherein the control unit is operable to trigger the activation signal that enables particle beam delivery at the requesting irradiation position.

4. The particle therapy device as claimed in claim 1, wherein the control unit is connected to an input of the assignment unit via a first permanently assigned signal connection, so that the presence of the request signal at the signal input unambiguously specifies the requesting irradiation position.

5. The particle therapy device as claimed in claim 1, wherein the assignment unit is operable to check an availability of the particle beam.

6. The particle therapy device as claimed in claim 1, wherein the assignment unit is operable to store a data table comprising the possible beam paths.

7. The particle therapy device as claimed in claim 1, wherein the accelerator control unit is operable to control the configuration of the configurable elements for the requested beam delivery.

8. The particle therapy device as claimed in claim 1, further comprising a permanently assigned signal connection from the assignment unit to the control unit, the signal connection being operable to transfer a confirmation signal between the assignment unit and the control unit of the requesting irradiation position.

9. The particle therapy device as claimed in claim 8, wherein the signal connections is a direct hardware connection.

10. The particle therapy device as claimed in claims 1, wherein at least two control units are individually connected, each via a permanently assigned signal connection and each to at least one output of the assignment unit.

11. The particle therapy device as claimed in claim 1, wherein the accelerator control unit and the at least one control unit are connected to a data bus system that is operable to exchange parameters of the particle beam, parameters of the accelerator and particle beam delivery unit that are specified by the control system with reference to a therapy schedule that forms the basis of the irradiation procedure, or both.

12. The particle therapy device as claimed in claim 1, wherein at least one of the at least two irradiation positions is a treatment position at which a patient is irradiated with the particles.

13. The particle therapy device as claimed in claim 1, wherein at least one of the at least two irradiation positions is a test position that is operable for checking parameters that characterize the particle irradiation.

14. A method for forming a beam path for an irradiation procedure in a particle therapy device which includes an accelerator and particle beam delivery unit operable to deliver particles to at least two irradiation positions and includes a control system operable to monitor and direct the particles along a particle beam path, wherein the control system comprises an assignment unit, a control unit arranged at each of the at least two irradiation positions and an accelerator control unit, the method comprising:
  initiating the irradiation procedure by communication between a control unit and the assignment unit, wherein a beam request signal and, following an assignment of the particle beam to the requesting irradiation position, a confirmation signal confirming the request are exchanged,
  transferring configuration parameters from the accelerator control unit to configurable elements of the accelerator and a beam transport unit, wherein the assigned control unit transfers information about the irradiation procedure to be carried out to the accelerator control unit, and
  activating the required elements specified by an activation signal from the assignment unit, when setting up the particle beam path, separately from the transferring, and implementing configuration parameters transferred from the accelerator control unit when the activation signal is present.

15. The method as claimed in claim 14, wherein activating the required elements take place concurrently with the transferring of configuration parameters.

16. The method as claimed in claim 15, wherein a "beam on" signal is transferred to the assignment unit during the initiating of the irradiation procedure, wherein the presence of the "beam on" signal in the assignment unit is a prerequisite for the execution of transferring of configuration parameters.

17. The method as claimed in claim 14, further comprising transporting particles along the formed beam path for irradiating in accordance with the irradiation procedure.

18. The particle therapy device as claimed in claim 1, further comprising a data bus system that is operable to transfer a confirmation signal between the assignment unit and the control unit of the irradiation position.

19. The particle therapy device as claimed in claim 1, further comprising an individual signal line connected between the control unit and the assignment unit.

20. The method as claimed in claim 14 wherein activating comprises authorizing operation of the required elements to act on a later received confirmation to deliver the particles.

21. The particle therapy device as claimed in claim 1, wherein the request signals and the activation signals are sent and received via specific unambiguous hardware connections.

22. The particle therapy device as claimed in claim 1, wherein the activation signals are present before and/or during the implementation of configuration parameters.

* * * * *